(12) United States Patent
Niddam-Hildesheim et al.

(10) Patent No.: US 6,777,552 B2
(45) Date of Patent: Aug. 17, 2004

(54) PROCESSES FOR PREPARING CALCIUM SALT FORMS OF STATINS

(75) Inventors: Valerie Niddam-Hildesheim, Even-Yeouda (IL); Revital Lifshitz-Liron, Herzlia (IL); Rami Lidor-Hadas, Kafar-Saba (IL)

(73) Assignee: Teva Pharmaceutical Industries, Ltd., Petach Tiqva (IL)

( * ) Notice: Subject to any disclaimer, the term of this patent is extended or adjusted under 35 U.S.C. 154(b) by 0 days.

(21) Appl. No.: 10/222,556

(22) Filed: Aug. 16, 2002

(65) Prior Publication Data

US 2003/0114685 A1 Jun. 19, 2003

Related U.S. Application Data

(60) Provisional application No. 60/312,812, filed on Aug. 16, 2001.

(51) Int. Cl.⁷ .................. C07D 207/325; C07D 209/04; C07D 239/40; C07D 309/30
(52) U.S. Cl. ...................... 544/332; 548/491; 548/537; 549/292
(58) Field of Search ........................................ 548/537

(56) References Cited

U.S. PATENT DOCUMENTS

| | | | |
|---|---|---|---|
| 4,231,938 A | 11/1980 | Monaghan et al. | |
| 4,346,227 A | 8/1982 | Terahara et al. | |
| 4,444,784 A | 4/1984 | Hoffman et al. | |
| 4,681,893 A | 7/1987 | Roth | |
| 4,739,073 A | 4/1988 | Kathawala | |
| 5,003,080 A | 3/1991 | Butler et al. | |
| 5,006,530 A | 4/1991 | Angerbauer et al. | |
| 5,011,930 A | 4/1991 | Fujikawa et al. | |
| 5,159,104 A | 10/1992 | Dabora et al. | |
| 5,177,080 A | 1/1993 | Angerbauer et al. | |
| 5,260,440 A | 11/1993 | Hirai et al. | |
| 5,273,995 A | 12/1993 | Roth | |
| 5,298,627 A | 3/1994 | Butler et al. | |
| 5,856,336 A | 1/1999 | Fujikawa et al. | |
| 5,872,130 A | 2/1999 | Fujikawa et al. | |
| 5,969,156 A | 10/1999 | Briggs et al. | |
| 6,002,021 A | 12/1999 | Yang et al. | |
| 6,100,407 A | 8/2000 | Van Dalen et al. | |
| RE37,314 E | 8/2001 | Hirai et al. | |
| 6,294,680 B1 | 9/2001 | Vries et al. | |
| 6,316,460 B1 | 11/2001 | Creekmore et al. | |
| 6,335,449 B1 | 1/2002 | Ohara et al. | |

FOREIGN PATENT DOCUMENTS

| | | |
|---|---|---|
| WO | WO 95/13283 | 5/1995 |
| WO | WO 99/30704 | 6/1999 |
| WO | WO 00/53173 | 9/2000 |
| WO | WO 00/53566 | 9/2000 |

OTHER PUBLICATIONS

Baumann, K.L. et al., Tet. Lett. 1992, 33, 2283–2284.
Brower, P.L. et al., Tet. Lett. 1992, 33, 2279–82.

Primary Examiner—Taofiq Solola
(74) Attorney, Agent, or Firm—Kenyon & Kenyon

(57) ABSTRACT

Processes for preparing a calcium salt of a statin from an ester derivative or protected ester derivative of the statin by using calcium hydroxide are provided. The ester or protected ester derivative is contacted with calcium hydroxide to obtain the calcium salt. Preferred statins are rosuvastatin, pitavastatin and atorvastatin, simvastatin and lovastatin. In processes beginning with a protected statin ester derivative, the protecting group is hydrolyzed during salt formation by contact with calcium hydroxide, or is contacted with an acid catalyst followed by contact with calcium hydroxide.

41 Claims, No Drawings

PROCESSES FOR PREPARING CALCIUM SALT FORMS OF STATINS

CROSS-REFERENCE TO RELATED APPLICATIONS

This application claims the benefit of provisional application Serial No. 60/312,812, filed Aug. 16, 2001 and U.S. patent application Ser. No. 10/037,412, filed Oct. 24, 2001, which claims the benefit of provisional application Serial No. 60/249,319, filed Nov. 16, 2000, all of which are incorporated herein by reference.

FIELD OF THE INVENTION

The present invention relates to processes for preparing calcium salt forms of statins.

BACKGROUND OF THE INVENTION

The class of drugs called statins are currently the most therapeutically effective drugs available for reducing low-density lipoprotein (LDL) particle concentration in the blood stream of patients at risk for cardiovascular disease and thus, statins are used in the treatment of hypercholesterolemia, hyperlipoproteinemia, and atherosclerosis. A high level of LDL in the bloodstream has been linked to the formation of coronary lesions that obstruct the flow of blood and can rupture and promote thrombosis. Goodman and Gilman, The Pharmacological Basis of Therapeutics, page 879 (9th Ed. 1996).

Statins inhibit cholesterol biosynthesis in humans by competitively inhibiting the 3-hydroxy-3-methyl-glutaryl-coenzyme A ("HMG-CoA") reductase enzyme. HMG-CoA reductase catalyzes the conversion of HMG to mevalonate, which is the rate determining step in the biosynthesis of cholesterol. Decreased production of cholesterol causes an increase in the number of LDL receptors and corresponding reduction in the concentration of LDL particles in the bloodstream. Reduction in the LDL level in the bloodstream reduces the risk of coronary artery disease. J.A.M.A. 1984, 251, 351–74.

Currently available statins include lovastatin, simvastatin, pravastatin, fluvastatin, cerivastatin and atorvastatin. Lovastatin (disclosed in U.S. Pat. No. 4,231,938) and simvastatin (ZOCOR; disclosed in U.S. Pat. No. 4,444,784 and WO 00/53566) are administered in the lactone form. After absorption, the lactone ring is opened in the liver by chemical or enzymatic hydrolysis, and the active hydroxy acid is generated. Pravastatin (PRAVACHOL; disclosed in U.S. Pat. No. 4,346,227) is administered as the sodium salt. Fluvastatin (LESCOL; disclosed in U.S. Pat. No. 4,739,073) and cerivastatin (disclosed in U.S. Pat. No. 5,006,530 and 5,177,080), also administered as the sodium salt, are entirely synthetic compounds that are in part structurally distinct from the fungal derivatives of this class that contain a hexahydronaphthalene ring. Atorvastatin and two new "superstatins," rosuvastatin and pitavastatin, are administered as calcium salts. The structural formulas of these statins are shown below.

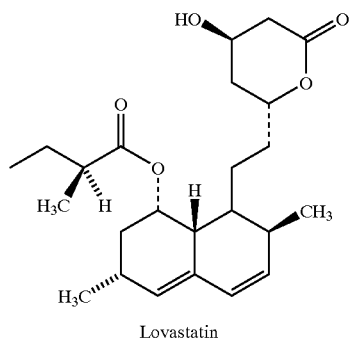

Lovastatin

Simvastatin

Pravastatin

Fluvastatin

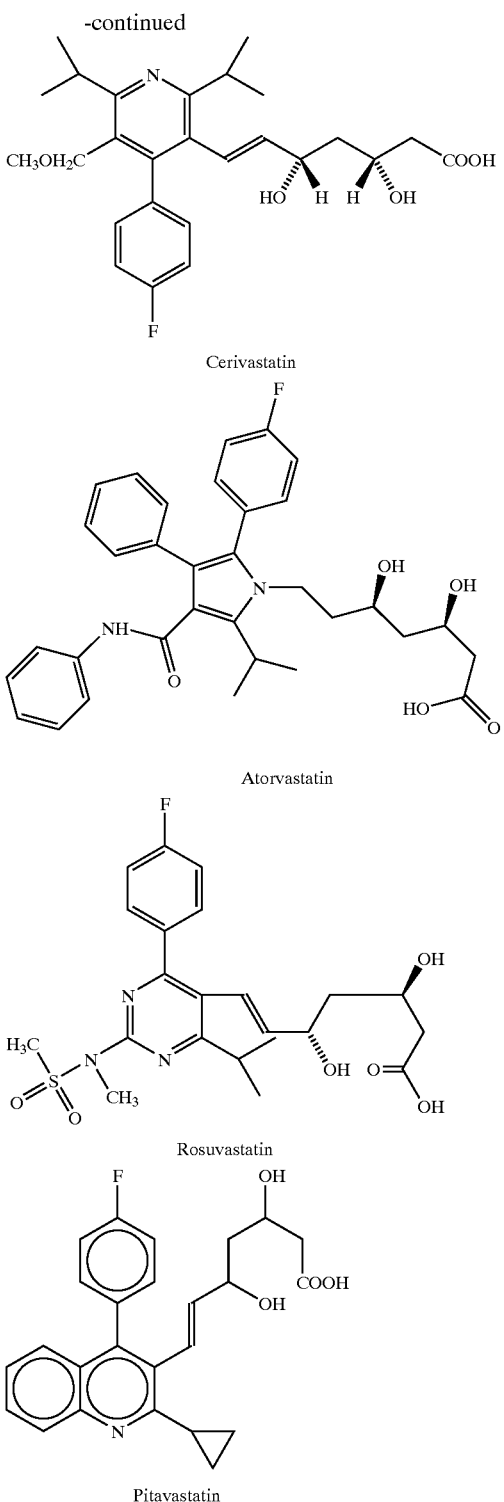

Cerivastatin

Atorvastatin

Rosuvastatin

Pitavastatin

Atorvastatin is the common chemical name for [R-(R*, R*)]-2-(4-fluorophenyl)-β,δ-dihydroxy-5-(1-methylethyl)-3-phenyl-4-[(phenylamino)carbonyl]-1H-pyrrole-1-heptanoic acid. The free acid of atorvastatin is prone to lactonization. The systematic chemical name of atorvastatin lactone is (2R-trans)-5-(4-fluorophenyl)-2-(1-methylethyl)-N,4-diphenyl-1-[2-tetrahydro-4-hydroxy-6-oxo-2H-pyran-2-yl) ethyl]-1H-pyrrole-3-carboxamide. Atorvastatin and its corresponding racemic lactone are disclosed in U.S. Pat. No. 4,681,893.

The lactone form is disclosed in U.S. Pat. No. 5,273,995. In Examples 4 and 5 of the '995 patent, the lactone is prepared by dissolving 1,1-dimethylethyl (R)-7-[2-(4-fluorophenyl)-5-(1-methylethyl)-3-phenyl-4-[(phenylamino)carbonyl]-1H-pyrrol-1-yl]-5-hydroxy-3-oxo-1-heptanoate in tetrahydrofuran and triethyl borane, followed by the addition of t-butylcarboxylic acid. After cooling, methanol is added followed by sodium borohydride. The mixture is poured into an ice/hydrogen peroxide/water mixture. Trichloromethane is added and the mixture is partitioned. The organic layer is dried over magnesium sulfate, filtered, and the solvent is evaporated. The product is dissolved in tetrahydrofuran and methanol and added to a solution of sodium hydroxide. The mixture is concentrated to remove organic solvent, added to water, and extracted with diethyl ether. The aqueous layer is acidified with hydrochloric acid and extracted with ethyl acetate. The organic layer is dried with anhydrous magnesium sulfate, filtered, and the solvent evaporated. The residue is dissolved in toluene and concentrated. The product is recrystallized from ethyl acetate and hexane to produce the lactone.

The lactone can also be prepared according to the procedures disclosed in U.S. Pat. No. 5,003,080. For instance, in Example 2, Method A, cis-2-(4-Fluorophenyl)-β,δ-dihydroxy-5-(1-methylethyl)-3-phenyl-4-(phenylamino)carbonyl-1H-pyrrole-1-heptanoic acid, methyl ester is treated with sodium hydroxide, and after dilution with water and separation, the remaining layer are washed with hexane and ethyl acetate followed by concentrated hydrochloric acid solution. Upon separation, the upper layer is washed with hydrochloric acid and concentrated. The residue is dissolved in toluene.

As disclosed in the '080 patent, the lactone can also be prepared by mixing (±)-cis-6-(2-aminoethyl)-2,2-dimethyl-1,3-dioxane-4-acetic acid (Example 2, Method B); (±)-(2α,4α,6α) or (±)-(2α,4β,6β)-6-(2-aminoethyl)-2-phenyl-1,3-dioxane-4-acetic acid (Example 2, Method C); (±)-cis-9-(2-aminoethyl)-6,10-dioxaspiro[4.5]decane-7-acetic acid (Example 2, Method D); (±)-cis-(4-(2-aminoethyl)-1,5-dioxaspiro[5.5]undecane-2-2acetic acid (Example 2, Method E); or (±)-(2α,4α,6α) or (±)-(2α,4β,6β)-6-(2-aminoethyl)-2-methyl-1,3-dioxane-4-acetic acid (Example 2, Method F and G) with (±)-4-fluoro-α-[2-methyl-1-oxopropyl]-γ-oxo-N,β-diphenylbenzenebutaneamide in dimethyl sulfoxide. After heating, the solution is poured into a mixture of diethyl ether and saturated ammonium chloride in water. After separation, the organic layer is washed with water and sodium hydroxide. The aqueous layer is acidified with dilute hydrochloric acid and extracted with ethyl acetate, to which hydrochloric acid is added, and the solution is concentrated. The residue is dissolved in toluene.

Another method of making the lactone, according to the '080 patent, includes mixing (+)-cis 1,1-dimethylethyl-6-(2-aminoethyl)-2,2-dimethyl-1,3-dioxane-4-acetate (Example 2, Method H); (±)-(2α,4α,6α) or (±)-(2α,4β,6β)-1,1-dimethyl-6-(2-aminoethyl)-2-phenyl-1,3-dioxane-4-acetate (Example 2, Method I); or (±)-cis-1,1-dimethylethyl (4-(2-aminoethyl)-1,5-dioxaspiro[5.5]undecane-2-acetate (Example 2, Method J) with (±)4-fluoro-α-[2-methyl-1-oxopropyl]-γ-oxo-N,β-diphenylbenzene butaneamide in heptane:toluene (9:1). After heating, the solution is poured into a mixture of tetrahydrofuran and ammonium chloride in water. After separation, the organic layer is washed with brine, followed by the addition of hydrochloric acid. After stirring, sodium hydroxide is added to the organic layer. The reaction is stopped by adding a mixture of water and hexane. After separation, the aqueous layer is acidified with dilute hydrochloric acid, extracted with ethyl acetate, and concentrated. The residue is dissolved in toluene.

The lactone or the free acid may be used to prepare the pharmaceutically acceptable calcium salt, [R-(R*,R*)]-2-(4-fluorophenyl)-β,δ-dihydroxy-5-(1-methylethyl)-3-phenyl-4-[(phenylamino)carbonyl]-1H-pyrrole-1-heptanoic acid calcium salt (2:1) trihydrate. In animal models, atorvastatin calcium salt has been shown to lower plasma cholesterol and lipoprotein levels by inhibiting HMG-CoA reductase and cholesterol synthesis in the liver. Atorvastatin is marketed by PFIZER as the hemicalcium salt trihydrate under the trade name LIPITOR, as 10, 20, 40 and 80 mg tablets. Atorvastatin hemicalcium salt has the following structure:

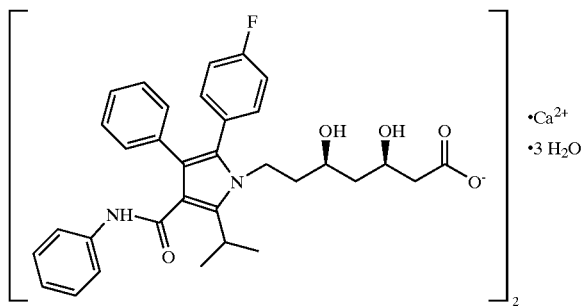

Atorvastatin Hemicalcium Salt

The hemicalcium salt is disclosed in U.S. Pat. No. 5,273,995, which teaches that the calcium salt is obtained by crystallization from a brine solution resulting from the transposition of the sodium salt with calcium chloride and further purified by recrystallization from a 5:3 mixture of ethyl acetate and hexane.

U.S. Pat. No. 5,298,627, also discloses a process for making the hemicalcium salt. In Example 1 of this patent, (4R-cis)-1-[2-[6-[2-(diphenylamino)-2-oxoethyl]-2,2-dimethyl-1,3-dioxan-4-yl]ethyl]-5-(4-fluorophenyl)-2-(1-methylethyl)-N,4-diphenyl-1H-pyrrole-3-carboxamide is dissolved in methanol and reacted with hydrochloric acid to form [R-(R*,R*)]-5-(4-fluorophenyl)-β,δ-dihydroxy-2-(1-methylethyl)-N,N,4-triphenyl-3-[(phenylamino)carbonyl]-1H-pyrrole-1-heptanamide, which is mixed with methanol and sodium hydroxide. The filtrate is washed with tert-butyl methyl ester and the aqueous layer is acidified using aqueous hydrochloric acid and extracted with tert-butyl methyl ester to form the sodium salt of [R-(R*,R*)]-2-(4-fluorophenyl)-β,δ-dihydroxy-5-(1-methylethyl)-3-phenyl-4-[(phenylamino)carbonyl]-1H-pyrrole-1-heptanoic acid. The sodium salt is converted to the hemicalcium salt by the addition of calcium acetate in water.

In an analogous process, (4R-cis)-6-(2-aminoethyl)-2,2-dimethyl-N,N-bis(phenylmethyl)-1,3-dioxane-4-acetamide is converted to [R-(R*,R*)]-5-(4-fluorophenyl)-β,δ-dihydroxy-2-(1-methylethyl)-4-phenyl-3-[(phenylamino)carbonyl]-N,N-bis(phenylmethyl)-1H-pyrrole-1-heptanamide which is further converted to the hemicalcium salt (Example 2); (4R-cis)-6-(2-aminoethyl)-N,N-diethyl-2,2-dimethyl-1,3-dioxane-4-acetamide is converted to [R-(R*,R*)]-N,N-diethyl-5-(4-fluorophenyl)-β,δ-dihydroxy-2-(1-methylethyl)-4-phenyl-3-[(phenylamino)carbonyl]-1H-pyrrole-1-heptanamide which is further converted to the hemicalcium salt (Example 3); (4R-cis)-6-(2-aminoethyl)-N-butyl-N,2,2-trimethyl-1,3-dioxane-4-acetamide is converted to [R-(R*,R*)]-N-butyl-5-(4-fluorophenyl)-β,δ-dihydroxy-N-methyl-2-(1-methylethyl)-4-phenyl-3-[(phenylamino)carbonyl]-1H-pyrrole-1-heptanamide which is further converted to the hemicalcium salt (Example 4); (4R-cis)-6-(2-aminoethyl)-N-(1,1-dimethylethyl)-2,2-dimethyl-N-(phenylmethyl)-1,3-dioxane-4-acetamide is converted to [R-(R*,R*)]-N-(1,1-dimethylethyl)-5-(4-fluorophenyl)-β,δ-dihydroxy-2-(1-methylethyl)-4-phenyl-3-[(phenylamino)carbonyl]-N-(phenylmethyl)-1H-pyrrole-1-heptanamide which is further converted to the hemicalcium salt (Example 5); and (4R-cis)-1-[[6-(2-aminoethyl)-2,2-dimethyl-1,3-dioxan-4-yl]-acetyl]piperidine is converted to [R-(R*,R*)]-1-[3,5-dihydroxy-7-oxo-7-(1-piperidinyl)heptyl]-5-(4-fluorophenyl-2-(1-methylethyl)-N-4-diphenyl-1H-pyrrole-3-carboxamide which is further converted to the hemicalcium salt (Example 6).

Rosuvastatin is the common chemical name for [S-[R*,S*-(E)]]-7-[4-(4-fluorophenyl)-6-(1-methylethyl)-2-[methyl(methylsulfonyl)amino]-5-pyrimidinyl]-3,5-dihydroxy-6-heptenoic acid. Rosuvastatin is in the process of being approved for marketing under the name CRESTOR, which contains rosuvastatin calcium. Rosuvastatin, its calcium salt (2:1), and its lactone form are disclosed and claimed in U.S. Pat. No. 5,260,440. The process of the '440 patent prepares rosuvastatin by reacting 4-(4-fluorophenyl)-6-isopropyl-2-(N-methyl-N-methylsulfonylamino)-5-pyrimidinecarbardehyde with methyl (3R)-3-(tert-butyldimethylsilyloxy)-5-oxo-6-triphenylphosphoranylidene hexanate in acetonitrile under reflux. The silyl group is then cleaved with hydrogen fluoride, followed by reduction with NaBH$_4$ to obtain a methyl ester of rosuvastatin.

The ester is then hydrolyzed with sodium hydroxide in ethanol at room temperature, followed by removal of ethanol and addition of ether, to obtain the sodium salt of rosuvastatin. The sodium salt is then converted to the calcium salt with a multi-step process. The sodium salt is dissolved in water and maintained under a nitrogen atmosphere. Calcium chloride is then added to the solution, resulting in precipitation of rosuvastatin calcium (2:1). Hence, the process of the '440 patent prepares rosuvastatin calcium through the sodium salt intermediate.

U.S. Pat. No. 6,316,460 discloses a pharmaceutical composition of rosuvastatin. The pharmaceutical compositions contain rosuvastatin or its salt and a multivalent tribasic phosphate salt. The '460 patent does not disclose any methods for preparing the calcium salt of rosuvastatin.

Pitavastatin is the common chemical name for (E)-3,5-dihydroxy-7-[4'-(4"-fluorophenyl)-2'-cyclopropyl-quinolin- 3'-yl]-hept-6-enoic acid. Pitavastatin, its calcium salt (2:1), and its lactone are disclosed in three related U.S. Pat. Nos. 5,011,930, 5,856,336 and 5,872,130.

The '930 patent prepares pitavastatin ethyl ester in accordance with Example 1. First 4-(4'-fluorophenyl-2'-(1'-cyclopropyl)-quinolin-3'-yl-carboxylate is prepared by reacting 2-amino-4'-fluorobenzophenone with ethyl isobutyrylacetate, which is then converted to 4-(4'-fluorophenyl)-3-hydroxymethyl-2-(1'-cyclopropyl)-quinoline, which is converted to 4-4'-fluorophenyl-2-(1'-cyclopropyl)-quinolin-3'-yl-carboxyaldehyde, which is converted to 3-(3'-ethoxy-1'-hydroxy-2'-propenyl)-4-(4'-fluorophenyl)-2-(1'cyclopropyl)-quinoline, which is converted to (E)-3-[4'-(4"-fluorophenyl)-2'-(1-cyclopropyl)-quinolin-3'-yl]propenaldehyde, which is converted to ethyl (E)-7-[4-(4"-fluorophenyl-2'-(1"-cyclopropyl)-quinolin-3'-yl]-5-hydroxy-3-oxohepto-6-enoate, which is converted to ethyl (E)-3,5-dihydroxy-7-[4'-(4"-fluorophenyl)-2'-(1"-cyclopropyl)-quinolin-3'-yl]-hept-6-enoate.

The resulting ester, ethyl (E)-3,5-dihodroxy-7-[4'-(4"-fluorophenyl)-2'-(1"-cyclopropyl)-quinolin-3'-yl]-hept-6-enoate, is converted to the sodium salt in accordance to Example 2 by using an aqueous solution of sodium hydroxide. The compound is dissolved in ethanol, to which an aqueous solution of sodium hydroxide is added. The resulting mixture is stirred and the ethanol is removed under reduced pressure. Water is then added, and the mixture is further extracted with ether. The aqueous layer is then lyophilized to obtain the final product, or the aqueous layer is weakly acidified with a dilute solution of hydrochloric acid. The acidified aqueous layer is then extracted with ether. After extraction, the ether layer is dried over magnesium sulphate. Then the ether is removed under reduced pressure to obtain the sodium salt. The '930 patent and its related patents do not disclose preparing the calcium salt of any compound.

These patents prepare the lactone by dissolving the sodium salt prepared in dry toluene, refluxing the solution and removing the toluene under reduced pressure. The crude solid is then recrystallized from diisopropyl ether to obtain the lactone, [4'-(4"-fluorophenyl)-2'-(1"-methylethyl) quinolin-3'-ylethynyl]-4-hydroxy-3,4,5,6-tetrahydro-2H-pyran-2-one. The lactone is further reduced using palladium/carbon under nitrogen atmosphere.

U.S. Pat. No. 6,335,449 improves the prior art process for preparing pitavastatin by reacting an aldehyde quinoline with diethyl cyanomthylphosphonate to obtain a nitrile intermediate for the synthesis of pitavastatin. U.S. Pat. No. 6,335,449 does not disclose how to prepare the calcium salt or any other salt of pitavastatin.

Simvastatin is the common medicinal name of the chemical compound butanoicacid,2,2-dimethyl-,1,2,3,7,8,8a-hexahydro-3,7-dimethyl-8-[2-(tetrahydro-4-hydro xy-6-oxo-2H-pyran-2-yl)-ethyl]-1-naphthalenyl ester, [1S*-[1a, 3a,7b,8b(2S*,4S),-8ab]]. (CAS Registry No. 79902-63-9.). Simvastatin is marketed as ZOCOR, and is disclosed in U.S. Pat. Nos. 4,444,784 and 6,002,021, as well as WO 00/53566. These references disclose preparing the lactone, and the open form of simvastatin.

Of these references, only WO 00/53566 discloses preparing the calcium salt of the open form of simvastatin. In a typical example, the process of WO 00/53566 hydrolyzes the lactone of simvastatin with sodium hydroxide, followed by addition of a calcium source, such as calcium acetate hydrate.

The above prior art processes of making calcium statin salts, such as atorvastatin, pitavastatin, rosuvastatin and simvastatin, all either do not disclose how to prepare the calcium salt, or proceed through a sodium salt intermediate. Further, some of the processes are highly sensitive and are not consistently reproducible and have unsuitable filtration and drying properties for large-scale production. It is desirable to obtain a stable product in fewer steps than previous methods using a process that is easily reproducible and is amenable to large-scale production.

SUMMARY OF THE INVENTION

The present invention provides a novel process for preparing statin calcium salts having the formula:

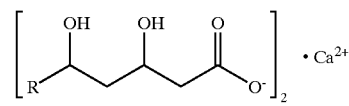

wherein R represents an organic radical, comprising contacting an ester derivative of the statin selected from the group consisting of:

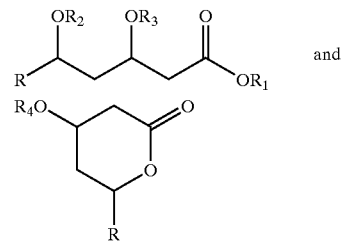

and with a sufficient amount of calcium hydroxide,
wherein $R_1$ is a $C_1$ to a $C_8$ alkyl group, and
$R_2$, $R_3$ and $R_4$ each independently represent hydrogen, or the same or different hydrolyzable protecting group, or $R_2$ and $R_3$, together with the oxygen atom to which each is bonded, form a hydrolyzable cyclic protecting group.

The reaction can be carried with or without a phase transfer catalyst. Preferred phase transfer catalysts are quaternary ammonium salts such as tetrabutylammonium bromide (TBAB) and triethylbenzylammonium chloride (TEBA). The reaction is preferably heated to accelerate the conversion.

Preferred statins are atorvastatin, rosuvastatin, pitavastatin and simvastatin. In a preferred embodiment, $R_2$, $R_3$ and $R_4$ are hydrogen. Each of $R_2$, $R_3$ or $R_4$ can also be the same or different protecting group, which are hydrolyzed by use of calcium hydroxide in one step together with hydrolysis of the ester group, i.e., —$COOR_1$, or hydrolyzed by using an acid catalyst, followed by hydrolysis of the ester group —$COOR_1$. Preferred protecting groups are silyl groups such as trialkylsilyl, which can be hydrolyzed by calcium hydroxide, and acetonide, which can be hydrolyzed by an acid catalyst. Acetonide forms a cyclic hydrolyzable protecting group, i.e., a dioxane.

In another aspect, the present invention provides a process for preparing a calcium salt of a statin having the formula:

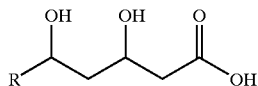

wherein R represents an organic radical, comprising the steps of:
adding calcium hydroxide and an ester derivative of the statin as described above to a mixture of water and a $C_1$ to a $C_4$ alcohol, heating the mixture, precipitating the calcium salt of the statin and separating the calcium salt.

DETAILED DESCRIPTION OF THE INVENTION

Forming an ester is a well known way of protecting a carboxylic acid group and masking its acidic proton. Green, T. W.; Wuts, P. G. M. Protective Groups in Organic Synthesis 3rd. ed., chapter 5 (John Wiley & Sons: New York 1999) ("Greene & Wuts"). It is also known, generally, that carboxylic acids that have been protected as esters may be deprotected by hydrolyzing the ester with a strong base. Id. at 377–78.

Sodium hydroxide is a strong base with a dissociation constant of 6.37 ($pK_b=-0.80$), Handbook of Chemistry and Physics 81st ed. 8–45 (CRC Press: Boca Raton 2000–01), and its use as a reagent for deprotecting ester-protected carboxylic acids is taught in the art. Green & Wuts, p. 377. Calcium hydroxide ($Ca(OH)_2$), with a first dissociation constant of $3.74 \times 10^{-3}$ ($pK_b=2.43$) and second dissociation constant of $4.0 \times 10^{-2}$ ($pK_b=1.40$), is a much weaker base than sodium hydroxide. Handbook of Chemistry and Physics 63rd ed. D-170 (CRC Press: Boca Raton 1983).

Calcium hydroxide is not listed among the reagents that have been used to hydrolyze esters in a well known compendium of functional group transformations in organic synthesis. Larock R. C. Comprehensive Organic Transformations 2nd ed., Section NITRILES, CARBOXYLIC ACIDS AND DERIVATIVES, Sub-sect. 9.17, pp. 1959–68 (Wiley-VCH: New York 1999). Its use as a general reagent for deprotecting ester-protected carboxylic acids is not taught by a well known reference book on methods for protecting and deprotecting organic functional groups. Greene & Wuts. pp. 377–79. In fact, U.S. Pat. No. 5,273,995 cautions against using an excess of sodium hydroxide to prepare the sodium salt in order to prevent forming calcium hydroxide when calcium chloride is later added to a solution of the sodium salt. It appears not to have been appreciated that ester-protected forms of statins such as atorvastatin can be converted directly to the respective hemi-calcium salts, such as atorvastatin hemi-calcium, without first treating the ester with a strong base like sodium hydroxide to hydrolyze it, then displacing the sodium ion by contacting the sodium salt with a calcium salt such as calcium chloride or calcium acetate.

As used herein, an "ester derivative" is a compound resulting from replacement of the hydroxyl proton of the carboxylic acid group in the ring-opened or dihydroxy acid form of the statin with a substituent bonded to the hydroxyl oxygen atom through carbon. Such ester derivatives include, e.g., compounds wherein the substituent bonded to the hydroxyl oxygen of the carboxylic acid is a $C_1-C_8$ alkyl group. The ester derivative used for conversion can be a mixture of derivatives containing various esters. For example, a methyl ester derivative can be added to ethanol, resulting in the conversion of some of the methyl esters to ethyl esters. The ester derivative of the statin can be produced by methods known in the art or can be purchased commercially. An ester derivative also includes the lactone or closed-ring form of the statin. The lactone form is a cyclic ester in which the ester group of the statin is incorporated into the ring. A mixture of ester derivatives also includes a mixture of the open- and closed-ring forms of the statin.

The present invention is directed to statins having the general formula:

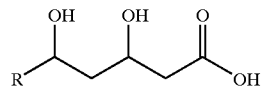

in which an organic radical R is attached to a diol-pentanoic acid group. These statins include, e.g., pravastatin, fluvastatin, cerivastatin, atorvastatin, rosuvastatin, pitavastatin, lovastatin and simvastatin. Of these, atorvastatin, rosuvastatin, pitavastatin and simvastatin are preferred.

R refers to an organic radical that is bonded to the diol pentanoic acid group. Depending on the statin, the R radical can be:
pravastatin: 1,2,6,7,8,8a-Hexahydro-6-hydroxy-2-methyl-8-(2-methyl-1-oxobutoxy)-1-naphthalene ethyl radical.
fluvastatin: 3-(4-fluorophenyl)-1-(1-methylethyl)-1H-indol-2-yl]-ethylene radical.
cerivastatin: 4-(4-fluorophenyl)-5-methoxymethyl)-2,6bis(1-methylethyl)-3-pyridinyl-ethylene radical.
atorvastatin: 2-(4-fluorophenyl)-5-(1-methylethyl)-3-phenyl-4-[(phenylamino)carbonyl]-1H-pyrrole-ethyl radical
rosuvastatin: [4-(4-fluorophenyl)-6-(1-methylethyl)-2-[methyl(methylsulfonyl)amino]-5-pyrimidinyl]-ethylene radical.
pitavastatin: [4'-(4"-fluorophenyl)-2'-cyclopropyl-quinolin-3'-yl]-ethylene radical.
The R radical can also be that of the open ring form, i.e., the dihydroxy acid, of simvastatin or lovastatin. These open ring forms also have a diol pentanoic acid group. As used herein, the terms simvastatin and lovastatin include both the lactone form and the open-ring form. When the statin is simvastatin or lovastatin, the R radical is:
simvastatin: 1,2,6,7,8,8a-Hexahydro-2,6-dimethyl-8-(2,2-dimethyl-1-oxobutoxy)-1-naphthalene ethyl radical.
lovastatin: 1,2,6,7,8,8a-Hexahydro-2,6-dimethyl-1-8-(2-methyl-l-oxobutoxy)-1-naphthalene ethyl radical.
The calcium salt of these and other statins can be made by the processes of the present invention such that the organic radical bonded to the diol pentanoic acid group or corresponding lactone, defines a compound that is a statin, i.e., a compound that inhibits 3-hydroxy-3-methyl-glutaryl-coenzyme A ("HMG-CoA") reductase enzyme. See e.g. WO 00/53566. Thus, R should not be construed as limited to the organic radical bonded to the diol pentanoic acid group or corresponding lactone of the statins expressly disclosed or exemplified herein. All hydrates, solvates and anhydrates of the calcium salt and other polymorphic forms thereof, crystalline or amorphous, of these statins are within the scope of the present invention.

The present invention illustrates preparation of calcium salt of these statins by using preparation of atorvastatin hemi-calcium as an example. To the extent that an aspect in the preparation of atorvastatin hemi-calcium is different than that for another statin, one of skill in the art would appreciate that atorvastatin is being used merely for illustrative purposes; and that the various aspects in the preparation of atorvastatin hemi-calcium can be readily modified to prepare the other statins, while still being within the spirit and scope of the present invention.

The present invention provides a process for preparing a statin hemi-calcium salt by converting a statin ester derivative of formula:

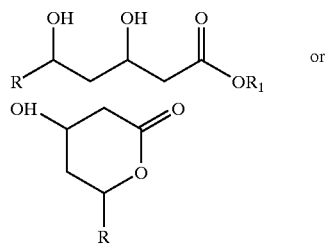

wherein R represents an organic radical and $R_1$ is a $C_1$ to $C_8$ alkyl group, to the corresponding hemi-calcium salt having the formula:

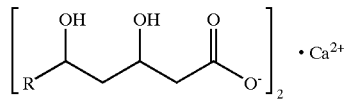

by contacting the ester derivative with a sufficient amount of calcium hydroxide. A "sufficient amount" as used herein refers to the amount of calcium hydroxide that substantially converts the ester derivative to the corresponding hemi-calcium salt. By "substantially converts" as used herein is meant an amount such that greater than about 50% (molar basis), preferably greater than about 70%, and more preferably greater than about 90% of the statin ester derivative is converted to the corresponding hemi-calcium salt. Most preferably, greater than about 95% of the statin ester derivative is converted to the corresponding hemi-calcium salt.

An unexpected advantage of this process is that the calcium hydroxide fulfills two roles. It functions as a basic catalyst for hydrolysis of the ester and supplies calcium ions for forming the hemi-calcium salt. Another significant practical advantage of the process is that the amount of calcium hydroxide does not have to be as carefully controlled as the amount of sodium hydroxide and calcium chloride/acetate used in other processes which, in contrast to the present invention, involve a sequential process of hydrolyzing the ester derivative with NaOH followed by displacement of the sodium ion with calcium ions.

The statin ester derivative may be provided in pure form or in mixture with other statin ester derivatives. The statin ester derivative, optionally in mixture with other statin ester derivatives, is dissolved or suspended preferably in a mixed solvent comprising a $C_1$–$C_4$ alcohol and water. Preferred alcohols are ethanol and isopropyl alcohol ("IPA") and a preferred solvent mixture contains about 5% to about 15% water in ethanol or IPA, more preferably about 10% water and about 90% ethanol (v/v) or IPA. Whether the statin ester derivative dissolves in the mixed solvent depends upon such factors as the choice of $C_1$–$C_4$ alcohol, the proportion of water, the temperature and the purity of the statin ester derivative. Calcium hydroxide is then suspended in the solvent and the base hydrolysis reaction mixture is maintained until the statin ester derivative has been consumed. Consumption of the statin ester derivative may be monitored by any conventional means such as TLC, HPLC and NMR. After the statin ester derivative has been consumed, statin hemi-calcium is recovered from the base hydrolysis reaction mixture by conventional means. It is unnecessary to add another source of calcium to provide a $Ca^{2+}$ ion for the atorvastatin hemi-calcium salt.

According to a preferred procedure for practicing the base hydrolysis process, the statin ester derivative is added in an amount sufficient to provide about 10 mmoles $L^{-1}$ to about 1 mole $L^{-1}$ of the mixed solvent.

Preferably, about 1 equivalent to about 6 equivalents of calcium hydroxide with respect to the ester derivative 1 is used. More preferably, from about 1 to about 2 equivalents is used.

Calcium hydroxide is only sparingly soluble in the $C_1$–$C_4$ alcohol:water mixed solvent and only a minor proportion of it will be in solution available to catalyze the hydrolysis at any one time. To accelerate the base hydrolysis, a phase transfer catalyst may be added to increase the solubility of the calcium hydroxide. Phase transfer catalysts are well known in the art and include, for instance, tetra-n-butylammonium bromide ("TBAB"), benzyltriethylammonium chloride ("TEBA"), tetra-n-butylammonium chloride, tetra-n-butylammonium bromide, tetra-n-butylammonium iodide, tetra-ethylammonium chloride, benzyltributylammonium chloride, benzyltributylammonium bromide, benzyltriethylammonium bromide, tetramethylammonium chloride and polyethylene glycol. A most preferred phase transfer catalyst is TBAB. When used, the phase transfer catalyst should be used in a substoichiometric amount, preferably from about 0.05 to about 0.25 equivalents, more preferably about 0.1 equivalents, with respect to statin ester derivative.

The mixture may be heated to up to the reflux temperature of the mixed solvent in order to accelerate the reaction. A preferred temperature range is at an elevated temperature of from about 40° C. to about 70° C.

After consumption of the statin ester derivative, statin hemi-calcium or solvate thereof is recovered from the base hydrolysis reaction mixture. As part of recovering the statin hemi-calcium, the reaction mixture is preferably filtered to remove excess suspended calcium hydroxide. The reaction mixture preferably is filtered while hot to prevent precipitation of statin hemi-calcium on the calcium hydroxide filtercake.

After filtration to remove suspended calcium hydroxide, statin hemi-calcium may be recovered from the filtrate by precipitation. According to a preferred recovery technique, statin hemi-calcium is caused to precipitate from the filtrate by slow addition of water. A volume of water roughly equivalent to the volume of the filtrate is added over about an hour's time. Preferably, the slow water addition is also conducted at elevated temperatures, e.g. from about 40° C. to about 65° C. Precipitating statin hemi-calcium by slow water addition yields statin hemi-calcium in a crystalline form and prevents formation of a gelatinous precipitate. Alternatively, statin hemi-calcium may be recovered by any conventional means. After any necessary purification steps, the recovered statin hemi-calcium may be used as an active ingredient to formulate a pharmaceutical product.

The filtering characteristics and purity of the statin hemi-calcium may be further improved by redissolving the crystalline product in the aqueous alcohol reaction mixture by heating to a temperature sufficient to cause all the precipitate to dissolve, resulting in a clear solution. The solution is preferably cooled slowly over several hours and held, preferably at ambient temperature, until no more crystals are observed to form. After filtering and drying, and any further optional purification steps, the statin hemi-calcium or solvate thereof may be used as an active ingredient in a pharmaceutical product.

Statins are sometimes prepared through an intermediate in which one or both of the hydroxyls in the pentanoic acid diol group (open-ring form) or the hydroxyl of the lactone (closed-ring form) are protected via a hydrolyzable protecting group and the carboxyl group is protected via an ester derivative as described hereinabove. For example, U.S. Pat. No. 5,260,440, incorporated herein by reference, uses a silyl protecting group during synthesis of rosuvastatin. U.S. Pat. Nos. 6,002,021 and 4,444,784, incorporated herein by reference, use a silyl protecting group during the synthesis of simvastatin. Brower, P. L. et al. *Tet. Lett.* 1992, 33, 2279–82 and Baumann, K. L. et al. *Tet. Lett.* 1992, 33, 2283–2284, incorporated herein by reference, prepare atorvastatin through a dioxane intermediate that has an acetonide protecting group, i.e., $R_2$ and $R_3$, together with the oxygen atom to which each is bonded, form a hydrolyzable cyclic protecting group.

These compounds, referred to herein as "protected statin ester derivatives" may be converted in accordance with the present invention to the corresponding hemi-calcium salt. Thus, in another embodiment, the present invention is directed to a process for preparing a calcium salt of a statin having the formula:

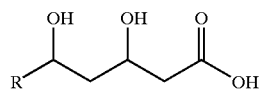

wherein R represents an organic radical, comprising contacting an ester derivative of the statin selected from the group consisting of:

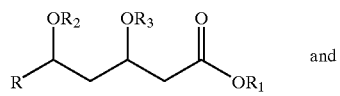 and

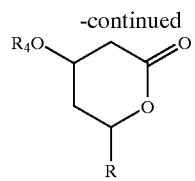

with a sufficient amount of calcium hydroxide, wherein $R_1$ is a $C_1$ to a $C_8$ alkyl group, and $R_2$, $R_3$ and $R_4$ each independently represent hydrogen, or the same or different hydrolyzable protecting group, or $R_2$ and $R_3$, together with the oxygen atom to which each is bonded, form a hydrolyzable cyclic protecting group. The protecting group used is preferably hydrolyzable under acidic or basic conditions. Preferred protecting groups $R_2$, $R_3$ and $R_4$ in accordance with this embodiment of the present invention include, for example, silyl groups, with trialkylsilyl and alkyldiarylsilyl being more preferred, and with t-butyl-dimethyl-silyl being the most preferred; and, cyclic protecting groups such that $R_2$ and $R_3$ form, for example, a dioxane.

U.S. Pat. No. 6,294,680, incorporated herein by reference, discloses additional protecting groups used in the synthesis of statins, particularly simvastatin. Disclosed cyclic protecting groups include a dioxane, a cyclic sulfate, a cyclic phosphate or borylidene, which are optionally substituted with alkyl and aryl groups. Other protecting groups include boronic acid, disclosed in WO 95/13283, incorporated herein by reference and esterification with an acetic anhydride, disclosed in U.S. Pat. No. 5,159,104, incorporated herein by reference. U.S. Pat. No. 6,100,407, incorporated herein by reference, discloses additional protecting groups. The protecting groups disclosed in these references may be used in accordance with the present invention.

It has surprisingly been found that a silyl group can be hydrolyzed and removed by contact with calcium hydroxide. Hence the use of a silyl group allows for removal of the protecting group and conversion of the ester to a calcium salt in one step, in the same solvent. The use of calcium hydroxide eliminates the need for a separate step of acid hydrolysis of the silyl protecting group with, e.g., a hydrogen halide such as hydrogen fluoride, to remove the protecting group, as required by the processes of U.S. Pat. Nos. 5,260,440 and 4,444,784. Thus, the process of the present invention applies to any statin with a silyl or other protecting group $R_2$, $R_3$ and $R_4$ capable of being hydrolyzed by calcium hydroxide. The protected rosuvastatin disclosed in U.S. Pat. No. 5,260,440, e.g., can be used, with a modification of reducing the ketone to obtain hydrogen as $R_2$. The silyl protected simvastatin disclosed in U.S. Pat. Nos. 4,444,784 and 6,002,021 can also be used.

Some of the protecting groups are best hydrolyzed under acidic conditions. Thus, before contacting the protected statin ester derivative with calcium hydroxide, an acid catalyst is added to hydrolyze the protecting group. Examples of such acid catalysts include acetic acid, trifluoroacetic acid, p-toluenesulfonic acid, zinc bromide and hydrochloric acid or other hydrogen halide, with acetic acid and hydrochloric acid being preferred. The resulting diol ester is then converted to the calcium salt by contact with calcium hydroxide. The process can also be carried out in one pot. The diol-ester is formed as described above, and is then reacted with calcium hydroxide to form atorvastatin hemi-calcium in the same pot, without changing solvent. A preferred solvent is a mixture of water and a $C_1$ to a $C_4$ alcohol, with ethanol being preferred. A preferred pH for the reaction is less than about 3, more preferably less than about 1.

A preferred protecting group that is removed with an acid catalyst is an acetonide, i.e., a compound in which the diol forms a cyclic hydrolyzable protecting group, i.e., a dioxane. Preferably, any acetone formed during the reaction of the acetonide with the acid catalyst is removed, e.g., by evaporation under reduced pressure.

The one pot process with use of acid catalyst is illustrated as follows:

Pharmaceutical compositions may be prepared as medicaments to be administered orally, parenterally, rectally, transdermally, bucally, or nasally. Suitable forms for oral administration include tablets, compressed or coated pills, dragees, sachets, hard or gelatin capsules, sub-lingual tablets, syrups and suspensions. Suitable forms of parenteral administration include an aqueous or non-aqueous solution or emulsion, while for rectal administration suitable forms for administration include suppositories with hydrophilic or hydrophobic vehicle. For topical administration, the invention provides suitable transdermal delivery systems known in the art, and for nasal delivery there are provided suitable aerosol delivery systems known in the art.

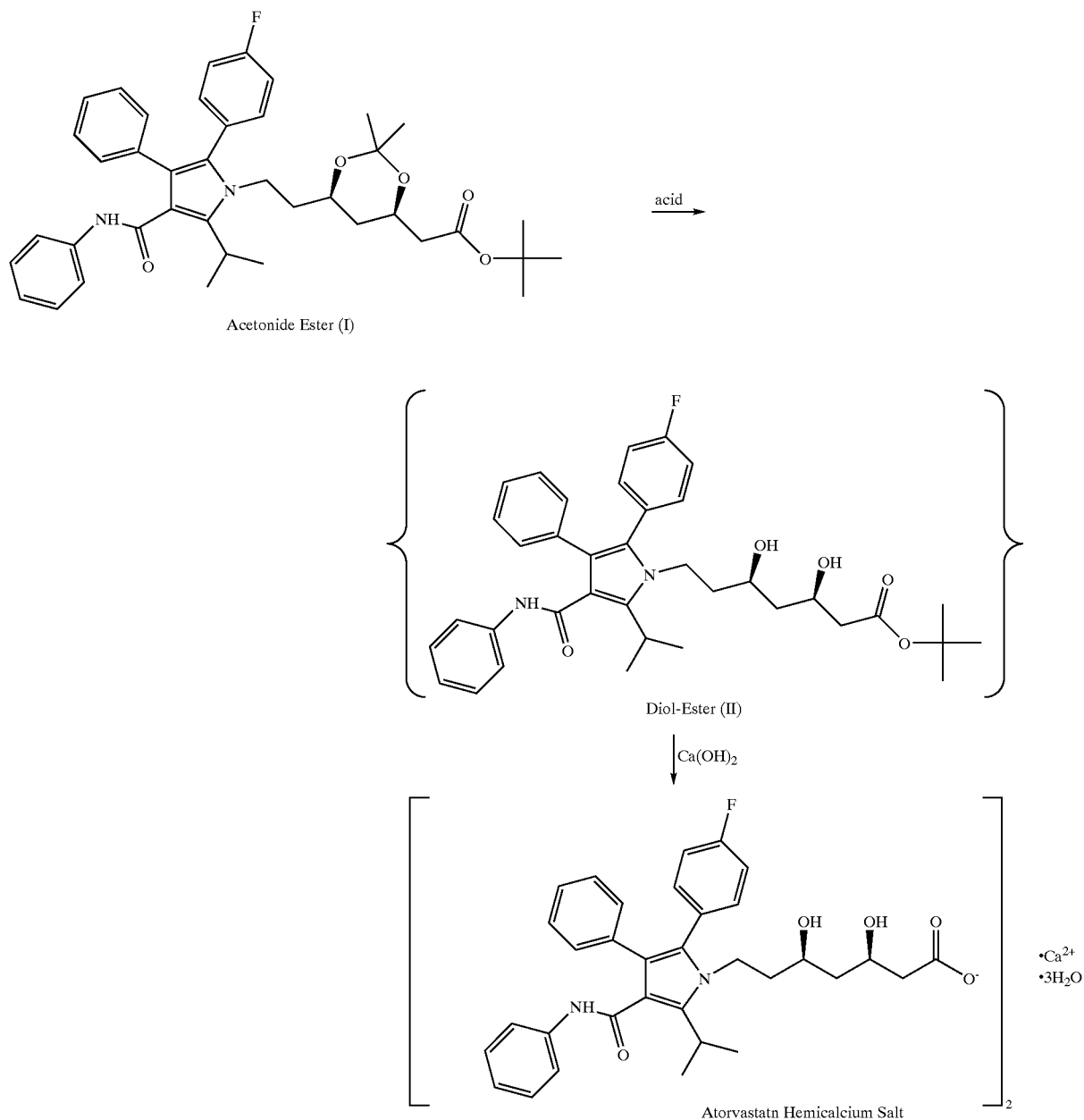

Pharmaceutical compositions of the present invention contain statin hemicalcium, particularly atorvastatin hemicalcium, rosuvastatin hemicalcium, pitavastatin hemicalcium, simvastatin hemicalcium and lovastatin hemicalcium. In addition to the active ingredient(s), the pharmaceutical compositions of the present invention can contain one or more excipients. Selection of excipients and the amounts to use can be readily determined by the formulation scientist based upon experience and consideration of standard procedures and reference works in the field. U.S. Pat. No. 6,316,460, incorporated herein by reference, and the most recent edition of Handbook of Pharmaceutical Excipients, American Pharmaceutical Association, can be used as a guidance. The dosage and formulation of LIPITOR® (atorvastatin hemi-calcium) and the other pharmaceuticals can also be used as a guidance.

EXAMPLES

General

Unless otherwise indicated, reagents were used as received. [R-(R*,R*)]-2-(4-fluorophenyl)-β,δ-dioxane-5-(1-methylethyl)-3-phenyl-4-[(phenylamino)carbonyl]-1H-pyrrole-1-tert-butylheptanoic ester (dioxane 2, $R_1$=t-Butyl) was prepared by a condensation reaction between the corresponding diketone and the corresponding chiral amine to form the pyrrole ring. It also may be prepared by known methods. Brower, P. L. et al. Tet. Lett. 1992, 33, 2279–82; Baumann, K. L. et al. Tet. Lett. 1992, 33, 2283–84. The following HPLC conditions were used to determine the composition of mixtures obtained in the acid hydrolyses reported in the examples: Waters Spherisorb S3 ODS1 (7.6×100 mm), 70:30 acetonitrile:water, 0.6 ml min.$^{-1}$, 20 µl sample, UV detection γ=254.

Example 1

Preparation of Atorvastatin Calcium From a Dioxane Ester Derivative

In a flask equipped with a magnetic stirrer, [R-(R*,R*)]-2-(4-fluorophenyl)-β,δ-dioxane-5-(1-methylethyl)-3-phenyl-4-[(phenylamino)carbonyl]-1H-pyrrole-1-tert-butylheptanoic ester (2.0 g) was suspended in an 80% aqueous solution of acetic acid (50 ml). The mixture was stirred at ambient temperature for about 20 hours until a clear solution was obtained. The clear solution was evaporated to dryness and the traces of acetic acid were removed by azeotropic distillation with toluene (3×50 ml) to obtain a powder.

The above obtained powder (200 mg, 0.32 10$^{-3}$ mole) was dissolved in ethanol (8 ml), to which a saturated solution of calcium hydroxide (8 ml) containing tetrabutyl ammonium bromide (10 mg) was added. The mixture was stirred and heated at a temperature of about 45° C., for about 24 hours. Additional saturated solution of calcium hydroxide (4 ml) was added. After about 20 minutes of stirring at ambient temperature, the reaction was completed. The purity of the resulting product was analyzed by HPLC. The white precipitate was filtered under vacuum and dried at a temperature of about 65° C. for about 18 hours. After drying, a 77% yield of atorvastatin calcium salt was obtained (142 mg).

Example 2

Preparation of Atorvastatin Calcium From a Dioxane Ester Derivative

In a flask equipped with a magnetic stirrer, [R-(R*,R*)]-2-(4-fluorophenyl)-β,δ-dioxane-5-(1-methylethyl)-3-phenyl-4-[(phenylamino)carbonyl]-1H-pyrrole-1-tert-butylheptanoic ester (10.0 g, 15.29 10$^{-3}$ mmole) was suspended in an 80% aqueous solution of acetic acid (150 ml). The mixture was stirred at ambient temperature overnight until a clear solution was obtained. The clear solution was evaporated and the traces of acetic acid were removed by azeotropic distillation with toluene (3×100 ml) to obtain an oily product containing toluene.

The oily product was placed in a mixture of ethanol (100 ml) and water (20 ml). A mixture of calcium hydroxide (5.5 eq., 6.22 g, 84.0 10$^{-3}$ mmole) and 5% (w/w of the dioxane ester derivative) tetrabutyl ammonium bromide (0.46 g) was added. The mixture was heated to a temperature of about 45° C. for about 3 hours until the reaction was completed. While the mixture was hot, filtration was done under vacuum to remove the excess calcium hydroxide. The mixture was then cooled to ambient temperature, after which, while stirring, water (200 ml) was added. After about 20 minutes of stirring at ambient temperature, the reaction was completed. The purity of the resulting product was analyzed by HPLC. The white precipitate was filtered under vacuum and dried at a temperature of about 65° C. for about 18 hours. After drying, an 84% yield of atorvastatin calcium salt was obtained (7.44 g).

Example 3

Preparation of Atorvastatin Lactone From a Dioxane Ester Derivative

To a flask equipped with a magnetic stirrer, [R-(R*,R*)]-2-(4-fluorophenyl)-β,δ-dioxane-5-(1-methylethyl)-3-phenyl-4-[(phenylamino)carbonyl]-1H-pyrrole-1-tert-butylheptanoic ester (0.5 g, 0.76 10$^{-3}$ mmole) was dissolved in a 1:1 mixture of trifluoroacetic-tetrahydrofuran (4 ml) in the presence of catalytic amount of water. The reaction mixture was stirred at ambient temperature for about 24 hours. The solution obtained was evaporated and the traces of trifluoroacetic were removed by azeotropic distillation with ether (3×10 ml). A white solid was obtained (0.3 g). Based on HPLC analysis, the white solid was a mixture of atorvastatin and atorvastatin lactone in the ratio of 40:60, respectively.

Example 4

Preparation of Atorvastatin Lactone From a Dioxane Ester Derivative

To a flask equipped with a magnetic stirrer, [R-(R*,R*)]-2-(4-fluorophenyl)-β,δ-dioxane-5-(1-methylethyl)-3-phenyl-4-[(phenylamino)carbonyl]-1H-pyrrole-1-tert-butylheptanoic ester (0.2 g, 0.30 10$^{-3}$ mmole) and zinc bromide (3.5 eq, 1.07 10$^{-3}$ mole) were dissolved in dichloromethane (5 ml). The reaction mixture was stirred at ambient temperature for about 24 hours. Water (30 ml) was added and the mixture was stirred for about 3 hours. The aqueous layer was extracted with dichloromethane (3×10 ml), whereas the organic layer was dried with sodium sulfate and filtrated. The organic layer was then evaporated under reduced pressure to give the resulting product (150 mg). Based on HPLC analysis, the resulting product was a mixture of atorvastatin and atorvastatin lactone in the ratio of 57:43, respectively.

Example 5
Preparation of Atorvastatin Lactone From a Dioxane Ester Derivative In a flask equipped with a magnetic stirrer, [R-(R*,R*)]-2-(4-fluorophenyl)-β,δ-dioxane-5-(1-methylethyl)-3-phenyl-4-[(phenylamino)carbonyl]-1H-pyrrole-1-tert-butylheptanoic ester (0.2 g) was suspended in a 90% aqueous solution of acetic acid (4 ml). The mixture was stirred at a temperature of about 50° C. for about 5 days. The resulting solution was evaporated to dryness and the traces of acetic acid were removed by azeotropic distillation with toluene (3×15 ml) to obtain a powder. Based on HPLC analysis, the product was a mixture of atorvastatin and atorvastatin lactone in the ratio of 54:46, respectively.

Example 6
Preparation of Atorvastatin Lactone From a Dioxane Ester Derivative In a flask equipped with a magnetic stirrer, a 3% aqueous solution of hydrochloric acid (1 ml) and [R-(R*,R*)]-2-(4-fluorophenyl)-β,δ-dioxane-5-(1-methylethyl)-3-phenyl-4-[(phenylamino)carbonyl]-1H-pyrrole-1-tert-butylheptanoic ester (0.2 g) were dissolved in methanol (2 ml). The mixture was stirred at a temperature of about 110° C. for about 4 hours and then stirred overnight at ambient temperature. The resulting solution was evaporated to dryness to obtain a powder. Based on HPLC analysis, the powder was a mixture of atorvastatin and atorvastatin lactone in the ratio 54:46, respectively.

Example 7
Preparation of Rosuvastatin Calcium From an Ester Derivative

In a flask equipped with a magnetic stirrer, methyl 7-[4-(4-fluorophenyl)-6-isopropyl-2-(N-methyl-N-methylsulfonylamino)pyrimidin-5-yl]-(3R,5S)-dihydroxy-(E)-6-heptenoate is dissolved in ethanol, to which a saturated solution of calcium hydroxide containing 5% (w/w of the ester derivative) tetrabutyl ammonium bromide is added. The mixture is stirred and heated at a temperature of about 45° C. for about 24 hours. Additional saturated solution of calcium hydroxide is added. After about 20 minutes of stirring at ambient temperature, the reaction is completed, resulting in rosuvastatin calcium.

Example 8
Preparation of Rosuvastatin Calcium From an Ester Derivative

In a flask equipped with a magnetic stirrer, methyl 7-[4-(4-fluorophenyl)-6-isopropyl-2-(N-methyl-N-methylsulfonylamino)pyrimidin-5-yl]-(3R,5S)-dihydroxy-(E)-6-heptenoate is placed in a mixture of ethanol and water. A mixture of calcium hydroxide and 5% (w/w of the ester derivative) tetrabutyl ammonium bromide is added. The mixture is heated to a temperature of about 45° C. for about 3 hours until the reaction is completed. While the mixture is hot, filtration is done under vacuum to remove the excess calcium hydroxide. The mixture is then cooled to ambient temperature, after which, while stirring, water is added. After about 20 minutes of stirring at ambient temperature, the reaction is completed, resulting in rosuvastatin calcium.

Example 9
Preparation of Pitavastatin Calcium From an Ester Derivative

In a flask equipped with a magnetic stirrer, ethyl (E)-3,5-dihydroxy-7-[4'-(4"-fluorophenyl)-2'-cyclopropyl-quinolin-3'-yl]-hept-6-enoate is dissolved in ethanol, to which a saturated solution of calcium hydroxide containing 5% (w/w of the ester derivative) tetrabutyl ammonium bromide is added. The mixture is stirred and heated at a temperature of about 45° C. for about 24 hours. Additional saturated solution of calcium hydroxide is added. After about 20 minutes of stirring at ambient temperature, the reaction is completed, resulting in pitavastatin calcium.

Example 10
Preparation of Pitavastatin Calcium From an Ester Derivative

In a flask equipped with a magnetic stirrer, ethyl (E)-3,5-dihydroxy-7-[4'-(4"-fluorophenyl)-2'-cyclopropyl-quinolin-3'-yl]-hept-6-enoate is placed in a mixture of ethanol and water. A mixture of calcium hydroxide and 5% (w/w of the ester derivative) tetrabutyl ammonium bromide is added. The mixture is heated to a temperature of about 45° C. for about 3 hours until the reaction is completed. While the mixture is hot, filtration is done under vacuum to remove the excess calcium hydroxide. The mixture is then cooled to ambient temperature, after which, while stirring, water is added. After about 20 minutes of stirring at ambient temperature, the reaction is completed, resulting in pitavastatin calcium.

Having thus described the invention with reference to particular preferred embodiments and illustrated it with Examples, those in the art can appreciate modifications to the invention as described and illustrated that do not depart from the spirit and scope of the invention as disclosed in the specification. The Examples are set forth to aid in understanding the invention but are not intended to, and should not be construed to, limit its scope in any way. The examples do not include detailed descriptions of conventional methods. Such methods are well known to those of ordinary skill in the art and are described in numerous publications. All references mentioned herein are incorporated in their entirety

What is claimed is:

1. A process for preparing a calcium salt of a statin having the formula:

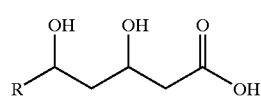

wherein R represents an organic radical, comprising contacting an ester derivative of the statin selected from the group consisting of:

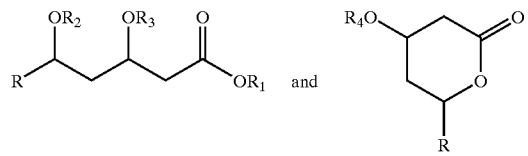

with a sufficient amount of calcium hydroxide, wherein $R_1$ is a $C_1$ to a $C_8$ alkyl group, and $R_2$, $R_3$ and $R_4$ each independently represent hydrogen, or the same or different hydrolyzable protecting group, or $R_2$ and $R_3$, together with the oxygen atom to which each is bonded, form a hydrolyzable cyclic protecting group.

2. The process of claim 1, wherein R is an organic radical from a statin selected from the group consisting of pravastatin, fluvastatin, cerivastatin, atorvastatin, rosuvastatin, pitavastatin, simvastatin and lovastatin.

3. The process of claim 2, wherein the statin is selected from the group consisting of atorvastatin, rosuvastatin, pitavastatin and simvastatin.

4. The process of claim 3, wherein the statin is rosuvastatin.

5. The process of claim 3, wherein the statin is pitavastatin.

6. The process of claim 3, wherein the statin is simvastatin.

7. The process of claim 3, wherein the statin is atorvastatin.

8. The process of claim 1, wherein the process is carried out in a mixture of water and a $C_1$ to a $C_4$ alcohol.

9. The process of claim 1, wherein the contacting is at elevated temperature.

10. The process of claim 1, wherein the contacting takes place in the presence of a phase transfer catalyst.

11. The process of claim 1, further comprising a step of recovering the calcium salt of the statin.

12. The process of claim 1, wherein $R_2$ and $R_3$ are both hydrogen.

13. The process of claim 1, wherein $R_4$ is hydrogen.

14. The process of claim 1, wherein at least one of $R_2$ or $R_3$ is a trialkylsilyl protecting group.

15. The process of claim 1, wherein $R_4$ is a trialkylsilyl protecting group.

16. The process of claim 1, further comprising a preliminary step of contacting the ester derivative, wherein the ester derivative has at least one protecting group, with an acid catalyst to hydrolyze the protecting group.

17. The process of claim 16, wherein the ester derivative has the formula:

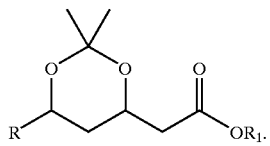

18. The process of claim 17, wherein R is an organic radical from atorvastatin.

19. A process for preparing rosuvastatin calcium salt comprising contacting a $C_1$ to a $C_8$ ester of 7-[4-(4-fluorophenyl)-6-iso-propyl-2-(N-methyl-N-methylsulfonylamino)pyrimidin-5-yl]-(3R,5S)-dihydroxy-(E)-6-heptenoate with a sufficient amount of calcium hydroxide.

20. A process for preparing rosuvastatin calcium salt comprising contacting lactone form of rosuvastatin with a sufficient amount of calcium hydroxide.

21. A process for preparing pitavastatin calcium salt comprising contacting a $C_1$ to a $C_8$ ester of (E)-3,5-dihodroxy-7-[4'-(4"-fluorophenyl)-2'-(1"-cyclopropyl)-quinolin-3'-yl]-hept-6-enoate with a sufficient amount of calcium hydroxide.

22. A process for preparing pitavastatin calcium salt comprising contacting lactone form of pitavastatin with a sufficient amount of calcium hydroxide.

23. A process for preparing a calcium salt of a statin having the formula:

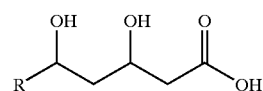

wherein R represents an organic radical, comprising the steps of:

a) adding calcium hydroxide and an ester derivative of the statin selected from the group consisting of:

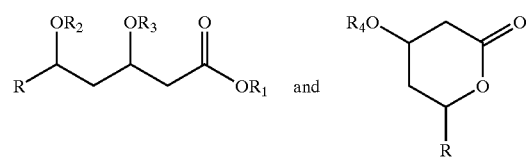

to a mixture of water and a $C_1$ to a $C_4$ alcohol, wherein $R_1$ is a $C_1$ to a $C_8$ alkyl group, and $R_2$, $R_3$ and $R_4$ each independently represent hydrogen, or the same or different hydrolyzable protecting group, or $R_2$ and $R_3$, together with the oxygen atom to which each is bonded, form a hydrolyzable cyclic protecting group;

b) heating the mixture;

c) precipitating the calcium salt of the statin; and d) separating the calcium salt.

24. The process of claim 23, wherein R is an organic radical from a statin selected from the group consisting of pravastatin, fluvastatin, cerivastatin, atorvastatin, rosuvastatin, pitavastatin, simvastatin and lovastatin.

25. The process of claim 24, wherein the statin is selected from the group consisting of atorvastatin, rosuvastatin, pitavastatin and simvastatin.

26. The process of claim 25, wherein the statin is rosuvastatin.

27. The process of claim 25, wherein the statin is pitavastatin.

28. The process of claim 25, wherein the statin is simvastatin.

29. The process of claim 25, wherein the statin is atorvastatin.

30. The process of claim 23, wherein $R_2$ and $R_3$ are both hydrogen.

31. The process of claim 23, wherein $R_4$ is a hydrogen.

32. The process of claim 23, wherein at least one of $R_2$ or $R_3$ is a trialkylsilyl protecting group.

33. The process of claim 23, wherein $R_4$ is a trialkylsilyl protecting group.

34. The process of claim 23, further comprising a preliminary step of contacting the ester derivative, wherein the ester derivative has at least one protecting group, with an acid catalyst to hydrolyze the protecting group.

35. The process of claim 34, wherein the ester derivative has the formula:

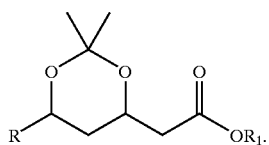

36. The process of claim 35, wherein R is an organic radical from atorvastatin.

37. The process of claim 23, wherein the mixture of water and the alcohol is from about a 5% to about a 20% mixture of water and alcohol (v/v).

38. The process of claim 23, further comprising adding a phase transfer catalyst to the mixture of step (a).

39. The process of claim 23, wherein the mixture is heated from about 40° C. to about 70° C.

40. The process of claim 23, further comprising a filtering step between steps (b) and (c).

41. The process of claim 23, wherein precipitating occurs by addition of water.

* * * * *

UNITED STATES PATENT AND TRADEMARK OFFICE
CERTIFICATE OF CORRECTION

PATENT NO. : 6,777,552 B2
DATED : August 17, 2004
INVENTOR(S) : Valerie Niddam-Hildesheim et al.

It is certified that error appears in the above-identified patent and that said Letters Patent is hereby corrected as shown below:

Column 6,
Line 42, change "pyrimidinecarbardehyde" to -- pyrimidinecarbaldehyde --.

Column 7,
Line 51, change "cyanomthylphosphonate" to -- cyanomethylphosphonate --.

Column 20,
Line 46, change "entirety" to -- entirety. --.

Signed and Sealed this

Thirty-first Day of May, 2005

JON W. DUDAS
*Director of the United States Patent and Trademark Office*